United States Patent
Zhong

(10) Patent No.: US 6,723,121 B1
(45) Date of Patent: Apr. 20, 2004

(54) POLYCARBONATE-POLYURETHANE DISPERSIONS FOR THROMBO-RESISTANT COATINGS

(75) Inventor: Sheng-Ping Zhong, Northboro, MA (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/671,418

(22) Filed: Sep. 27, 2000

Related U.S. Application Data

(63) Continuation of application No. 09/248,307, filed on Feb. 11, 1999, now Pat. No. 6,197,051, which is a continuation of application No. 08/877,987, filed on Jun. 18, 1997, now abandoned.

(51) Int. Cl.$^7$ .................................................. A61F 2/06
(52) U.S. Cl. ....................... 623/1.46; 604/266; 427/2.25
(58) Field of Search ............................... 623/1.46, 2.42, 623/66.1, 921, 926; 606/191, 198; 604/266; 427/2.25; 524/389

(56) References Cited

U.S. PATENT DOCUMENTS

| | | |
|---|---|---|
| 4,119,094 A | 10/1978 | Micklus et al. |
| 4,844,976 A * | 7/1989 | Huang ........................ 428/323 |
| 4,994,167 A * | 2/1991 | Shults et al. ........... 204/403.05 |
| 5,037,677 A | 8/1991 | Halpern et al. |
| 5,041,100 A | 8/1991 | Rowland et al. |
| 5,049,393 A | 9/1991 | Noon et al. |
| 5,133,742 A | 7/1992 | Pinchuk |
| 5,163,958 A | 11/1992 | Pinchuk |
| 5,263,992 A | 11/1993 | Guire |
| 5,272,012 A | 12/1993 | Opolski |
| 5,282,823 A | 2/1994 | Schwartz et al. |
| 5,342,348 A | 8/1994 | Kaplan |
| 5,342,621 A | 8/1994 | Eury |
| 5,360,397 A | 11/1994 | Pinchuk |
| 5,383,928 A | 1/1995 | Scott et al. |
| 5,449,382 A | 9/1995 | Dayton |
| 5,464,450 A | 11/1995 | Buscemi et al. |
| 5,496,581 A | 3/1996 | Yianni et al. |
| 5,541,167 A | 7/1996 | Hsu et al. |
| 5,571,166 A | 11/1996 | Dinh et al. |
| 5,575,818 A | 11/1996 | Pinchuk |
| 5,591,224 A | 1/1997 | Schwartz et al. |
| 5,599,352 A | 2/1997 | Dinh et al. |
| 5,741,881 A | 4/1998 | Patnaik |
| 5,798,409 A * | 8/1998 | Ho ............................. 524/506 |
| 6,001,067 A * | 12/1999 | Shults et al. ................ 600/584 |
| 6,099,563 A * | 8/2000 | Zhong ....................... 623/1.46 |
| 6,197,051 B1 * | 3/2001 | Zhong ....................... 623/1.46 |

FOREIGN PATENT DOCUMENTS

| | | |
|---|---|---|
| EP | 496 305 A2 | 7/1992 |
| EP | 627 226 A1 | 12/1994 |
| EP | 728 487 A1 | 8/1996 |
| WO | WO 91/19756 | 12/1991 |
| WO | WO 92/19289 | 11/1992 |
| WO | WO 92/19290 | 11/1992 |

* cited by examiner

Primary Examiner—Paul B. Prebilic
(74) Attorney, Agent, or Firm—Kenyon & Kenyon

(57) ABSTRACT

A coating for a medical device is described which enhances the bio-activity of the surface of a medical device, rendering the surface substantially bio-compatible. The bio-compatible coating is formed from a composition which includes an aqueous emulsion or dispersion of a polycarbonate-polyurethane composition and an excess of polyfunctional cross-linking agent.

6 Claims, No Drawings

POLYCARBONATE-POLYURETHANE DISPERSIONS FOR THROMBO-RESISTANT COATINGS

The present invention is a continuation of U.S. application Ser. No. 09/248,307 filed Feb. 11, 1999, now U.S. Pat. No. 6,197,051, which itself is a continuation of application number 08/877,987 filed Jun. 18, 1997 which is now abandoned.

FIELD OF INVENTION

This invention relates generally to medical devices having bio-compatible substrate coatings. More particularly, the present invention relates to an implantable medical device or a part thereof which has a bio-compatible coating for enhancing the biostability of the device. Such a coating can also serve as a primer for a second coating layer which contains certain bio-active agents. Coatings and methods for incorporating such coatings onto the surface of medical devices are also described.

BACKGROUND OF THE INVENTION

It is generally known to provide a substrate, such as a medical device or parts of such a device with various types of coatings for enhancing the biocompatability of the device when it is introduced into a mammal, such as a human body.

In particular, implantable medical devices used for minimally invasive procedures in body conduits, such as for example in blood vessels, the esophagus or urethra may be provided with bio-compatible coatings. Among the various intraluminal prostheses commonly used today are vascular grafts which include endovascular grafts, stents and graft-stent combinations. Various types of stents are available such as wire stents and tubular stents. These constructions may be made from metals or polymers and may be of the balloon expandable type or the self-expanding type. Among the self-expanding type are those made from superelastic, shape-memory materials such as nitinol. Other devices which can benefit from such coatings include catheters, guide wires, trocars, introducer sheaths and the like.

Medical devices coated with bio-compatible coatings and methods for providing substrates with such coatings have been described in a number of references, some of which are described below.

Various biocompatible coatings have been employed with medical devices in an attempt to impart enhanced bio-compatibility and other properties to such devices. For example, therapeutic agents have been incorporated into polymeric films made from polyurethane, polyester, polylactic acid, polyamino acid, polyorthoester, polyphosphate ester and the like, as disclosed in U.S. Pat. No. 5,282,823. U.S. Pat. No. 5,163,958 discloses a stent having a binder layer and an anti-thrombogenic pyrolytic amorphous carbon layer attached to the binder layer to provide an anti-thrombogenic surface.

Biologically active agents have been incorporated into polymeric films for slow or controlled release of the active agent into the body. For example, U.S. Pat. No. 5,342,348 discloses porous polyurethane and PTFE stents having bio-degradable polymeric filaments attached thereto which release drug over time. U.S. Pat. No. 5,383,928 discloses delivery of a drug using a stent-sheath structure made from both degradable and non-degradable polymers, such as ethylene vinyl acetate (EVA).

Endoprostheses have also been developed for targeted drug delivery to sites within a body. Such endoprostheses can be coated with microporous materials having pores in which bio-active agents may be anchored for controlled delivery thereof over time. In particular, U.S. Pat. No. 5,449,382 to Dayton (hereinafter the "'382 patent") discloses a minimally invasive bio-activated endoprosthesis for vessel repair. This endoprosthesis is coated with a polymer having a microporous structure with a predetermined pore size and a bio-active substance disposed within these pores for elution therefrom. The coating described by the '382 patent is made from a polymeric solution which includes silicone, polyurethane, polyvinyl alcohol, polyethylene, biodegradable polylactic acid polymers, polyglycolic acid polymers, polyesters, hydrogeels, tetrafluoroethylene, pollytetrafluoroethylene, fluorosilicone etc. Admixed into one of these polymers is a bio-active agent, such as for example heparin, for controlled and prolonged release thereof.

One drawback to conventional biocompatible coatings is the use of organic solvents. Such organic solvents may be highly reactive in vivo if not completely removed prior to implantation. Furthermore, in instances where the bio-active agent is admixed with the polymer, the surface of the article coated with such a composition is not necessarily continuously bio-active, i.e., active throughout the entire surface. Thus, such a coating may be less effective at preventing, e.g., thrombosis formation, than coatings which are designed to provide resistance to thrombosis throughout the surface.

Although polyurethane coatings have been employed as biomaterials, they are known to suffer from stability problems and such coatings are quickly bio-degraded and or bio-eroded. Thus, attempts have been made to develop medical devices and polyurethane coatings therefor which contain compositions which are less susceptible to biodegradation and bio-erosion.

In particular, U.S. Pat. No. 5,133,742 to Pinchuk (hereinafter the "'742 patent") discloses a prosthesis formed from polycarbonate-urethane polymers. Such polycarbonate-urethane compositions are bio-compatible and less susceptible to biodegradation and/or bio-erosion than simple polyurethane coatings. The '742 patent describes forming the polycarbonate-urethane polymer from the reaction of a polycarbonate diol, a diisocyanate and a chain extender in a suitable organic solvent. This polymer is then spun through a spinnerette into a filamentous vascular graft. Prostheses formed entirely from such a composition, however, are expensive to produce.

U.S. Pat. No. 5,575,818 to Pinchuk discloses a locking ring or barb-type braided stent coated or lined with porous bio-compatible coating materials which include polyurethane, spun polyurethane, spun polycarbonate urethane, spun polyolefin, silicone coated polyurethane, spun silicone and combinations thereof. This patent, however, suffers from the drawback, that most of the materials, including the spun polycarbonate urethane coatings or linings are applied in a non-efficient, labor intensive manner. In particular, the preferred method for forming the liner or coating includes spinning the polymer on a mandrel at an angle coincident with the pitch angle of the stent (i.e., the pitch angle of the stent's body section, as well as, the locking ring ends thereof). The lining is then applied to an adhesive-covered stent.

EP Publication No. 627 226 to Severini (hereinafter the "Severini publication") also describes a stent which is coated with a polycarbonate-urethane composition. This coating composition, however, suffers from the drawback that it is applied to the stent as a segmented thermoplastic polycarbonate-urethane solution containing an organic solvent, such as dimethylacetarnide. A stent coated with such a composition is clearly not desirable because of the danger to the patient should all of the organic solvent not be evaporated prior to implantation. Furthermore, the evaporation of organic solvents, such as dimethylacetarnide, not only increases the health risks to manufacturing personnel but also pollutes the environment. Moreover, the required evaporation step adds a significant amount of time to the coating process, i.e., 24 hours. Still further, in the Severini publication, the process of applying the polycarbonate-urethane coating to the stent is slow and inefficient. In particular, the process includes rotating the stent at a speed of 2 rpm while the coating is dripped onto the stent from a pipette suspended thereover. Coatings formed in such a manner are unequal and nonuniform.

The present invention is directed to aqueous dispersions or emulsions of polycarbonate-polyurethane coatings for implantable devices and methods of preparation thereof. These coatings are particularly advantageous because they make it possible to impart implantable devices with long-term biostability and such coatings serve as superior primer layers for attachment of optional bio-active agents. Furthermore, due to the aqueous-based nature of the coatings of the present invention, they are less hazardous than the prior art coatings cited hereinabove. Moreover, these coatings are highly versatile and can be efficiently applied to a wide range of substrates including heat sensitive substrates, such as, polyethyleneterphlate (PET) balloon catheters and stents. Because the optional bio-active agents of the present invention are covalently bonded to the polycarbonate-polyurethane primer, the bio-active agents are permanently attached to the substrate unlike certain of the transient coatings discussed above.

In summary, all of the references cited above suffer from the drawback that they use organic solvents in their coating layer and/or cure at high temperatures. Thus, there is a need for improved bio-compatible coatings which enhance the biostability, abrasion-resistance, lubricity and bio-activity of the surface of implantable medical devices, especially heat sensitive medical devices and coatings which have heat-sensitive biomolecules. In particular, there is a need for improved, cost efficient compositions and devices which have antithrombogenic properties and for more efficient methods of providing same. The present invention is directed to meeting these and other needs.

SUMMARY OF THE INVENTION

In one embodiment of the present invention there is provided a medical device having on a surface thereof a continuous bio-compatible coating. This bio-compatible coating is formed from an aqueous emulsion or dispersion of a polycarbonate-polyurethane composition containing one or more internal emulsifying agents.

In another embodiment of the present invention, there is provided a process for rendering a medical device bio-compatible. This process includes providing a substrate with a coating which contains an aqueous emulsion or dispersion of a polycarbonate-polyurethane composition having at least one internal emulsifying agent. The coating is then dried onto the substrate to attach the coating to said substrate.

In a farther embodiment of the present invention, there is provided a coating for enhancing the bio-activity of a surface of a medical device. This coating is formed from an aqueous emulsion or dispersion which includes a polycarbonate-polyurethane composition containing an organic acid functional group and an excess of a polyfunctional cross-linking agent. This composition forms a coating on a surface of the medical device and is reactive with thrombo-resistant agents.

In yet a further embodiment of the present invention, there is provided a medical device with enhanced thrombo-resistance. This medical device includes a substrate having a surface to which a continuous thrombo-resistant coating may be attached. The thrombo-resistant coating contains an aqueous emulsion or dispersion of a polycarbonate-polyurethane composition containing an internal emulsifying agent. This composition is attached to the substrate surface.

In another embodiment, a medical device is provided which has a surface which is rendered bio-compatible by means of a first coating layer. This coating layer includes a layer of a polycarbonate-polyurethane composition which contains an internal emulsifying agent.

In still a further embodiment, there is provided a medical device which has a surface coated with a bio-active layer. This bio-active layer is the reaction product of a polycarbonate-polyurethane first layer which contains an internal emulsifying agent and a polyfunctional cross-linking agent and a bio-active agent second layer which has at least one organic acid functional group.

DETAILED DESCRIPTION OF THE INVENTION

The present invention is directed to medical devices having bio-compatible coatings attached to a surface thereof. These bio-compatible coatings are formed from an aqueous emulsion or dispersion of a polycarbonate-polyurethane composition containing one or more internal emulsifying agents. Specifically, the internal emulsifying agents may comprise one or more organic functional groups selected from the group consisting of free carboxylic acid, free sulfonic acid, free phosphoric acid and combinations thereof. Such coatings alone are sufficient to provide a medical device with a bio-compatible surface. To augment such a bio-compatible coating, a second coating layer may be applied over the polycarbonate-polyurethane coating composition. When such augmentation is desired, it is preferred that the internal emulsifier in the polycarbonate-polyurethane composition contain one or more organic acid functional groups or metal salts thereof. When such augmentation is not desired, however, the internal emulsifying agent in the polycarbonate-polyurethane composition can be any internal emulsifier known in the art which is compatible with the intended use of the present invention.

For purposes of the present invention, the term "organic acid functional group" is meant to include any functional group which contains an organic acidic ionizable hydrogen. Examples of such functional groups include free carboxylic, free sulfonic, and free phosphoric acid groups, their metal salts and combinations thereof. Such metal salts include, for example, alkali metal salts like lithium, sodium and potassium salts; alkaline earth metal salts like calcium or magnesium salts; and quaternary amine salts of such acid groups, particularly quaternary ammonium salts.

In the present invention, the organic acid functional group-containing polycarbonate-polyurethane composition is selected based on the nature of the substrate to be coated. Such compositions are aqueous based and provide enhanced biostability to the surface of a medical device over conventional polyurethane coatings. Furthermore, such compositions have increased bio-compatibility and are environmentally friendly because traditionally used organic solvents are not required in order to apply the composition of the present invention to the surface of a medical device. Moreover, because these compositions are aqueous-based, they can be applied to a wide variety of substrates without concern for attack of a solvent on the substrate.

Polycarbonate-polyurethane aqueous dispersions and/or emulsions useful in the present invention include those which are commercially available from Zeneca Resins under the trade names NeoRez R-985 (aliphatic polycarbonate diol) and NeoRez R-986 (aliphatic polycarbonate diol); from Industrial Copolymer Ltd. under the trade names W830/048 (polycarbonate backbone), W830/092 (modified polycarbonate background), W830/140 (polycarbonate backbone) and W830/256 (polycarbonate background); and from Miles Inc. (Bayer AG) under the trade names Bayhydrol 121 (anionic dispersion of an aliphatic polycarbonate urethane polymer in water and n-methyl-2-pyrrolidone with a tensile strength of 6700 psi and an elongation at break of 150%) and Bayhydrol 123 (anionic dispersion of an aliphatic polycarbonate urethane polymer in water and n-methyl-2-pyrrolidone with a tensile strength of 6000 psi and an elongation at break of 320%).

In the present invention, the useful concentration of the polycarbonate-polyurethane aqueous emulsion or dispersion is from about 0.1% to about 60% by weight, and preferably from about 1% to about 20% by weight. These percent weight values are calculated based on the amount of solid polymer compared to the total weight of the first coating.

When it is desired to augment the first polycarbonate-polyurethane coating with a second coating containing a bio-active agent, the polycarbonate-polyurethane aqueous emulsion or dispersion optionally includes one or more polyfunctional cross-linking agents that are reactive with organic acid functional groups, including those functional groups functioning as internal emulsifiers on the polycarbonate-polyurethane composition of the present invention. Various polyfunctional cross-linking agents may be used. In the present invention, preferred polyfunctional cross-linking agents include polyfunctional aziridines and polyfunctional carbodiimides.

Furthermore, in the present invention, other cross-linking agents may also be used which include, for example, commercially available preparations sold by Zeneca Resins under the trade name NeoCryl CX 100 and those preparations sold by EIT Industries under the trade name XAMA-7. A commercially available polyfunctional carbodiimide which is also useful in the present invention is Ucarlink XL-29SE, sold by Union Carbide.

Among the polyfunctional aziridines particularly useful in the present invention are the trifunctional aziridines of the following formula:

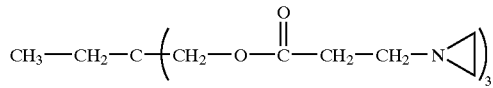

Preferably, the cross-linking agent has more than two functional groups per molecule. Furthermore, the present invention also encompasses a combination of different polyfunctional cross-linking agents.

Not wishing to be bound by a particular theory, it is believed that the functional groups on the cross-linking agent serve at least two purposes. In particular, these groups serve to cross-link the polycarbonate-poly-urethane composition when the internal emulsifier contains an organic acid functional group. Additionally, these groups on the cross-linking agent participate in covalently bonding a second coating composition containing a bio-active agent which has one or more organic acid functional groups to the polycarbonate-polyurethane composition through the excess organic acid functional groups on the polyfunctional cross-linking agent. Thus, there must be sufficient functionality in the cross-linking agent, e.g. an excess of cross-linking agent, to accomplish both purposes. In particular, there must be a molar excess of cross-linking agent relative to the polycarbonate-polyurethane composition to ensure that it is substantially cross-linked, and that there are enough unreacted functional groups left on the cross-linking agent to covalently bond the bio-active agent to the polycarbonate-polyurethane composition.

One indication that insufficient functional groups from the optional cross-linking agent are present is the inadequate bonding of the optional bio-active agent to the surface of the medical device. This is evidenced by the lack of bio-activity on the surface of medical devices treated with such a deficient polycarbonate-polyurethane composition.

The concentration of the optional cross-linking agent in the polycarbonate-polyurethane composition is in the range from about 0.2% to about 30% by weight, and preferably in the range from about 0.5% to about 20% by weight.

The aqueous polycarbonate-polyurethane composition may include other conventional additives, such as for example, leveling agents, various stabilizers, pH adjustment agents, defoaming agents, thickening agents, fillers, and the like, as long as, such agents are compatible with the intended use of the coated substrate.

The polycarbonate-polyurethane composition is applied to a substrate, i.e., an implantable medical device, by conventional methods, including dipping and spraying. This composition is then dried to obtain a continuous, thrombo-resistant, substantially water-insoluble coating on the surface of the medical device. Thus, the polycarbonate-polyurethane composition alone is able to effectively function as a thrombo-resistant top coat for implantable medical devices. As set forth above, when the polycarbonate-polyurethane composition is used alone, any internal emulsifying agent may be used which is compatible with the intended medical uses of the present invention. The selection of such internal emulsifying agents is well within the knowledge of one skilled in the art.

If, however, it is desired to modify and/or augment the final properties of an implantable medical device coated with the present polycarbonate-polyurethane top coat, it is a simple matter to modify this composition to function as a binder for a second coating layer which contains a bio-active agent as described in more detail below. In particular, when a bio-active agent coating is to be applied over the polycarbonate-polyurethane coating, the internal emulsifying agent must contain at least one organic acid functional group or similar functioning moiety. A polyfunctional cross-linking agent as described above is then added to the polycarbonate-polyurethane coating composition.

This modified polycarbonate-polyurethane aqueous emulsion or dispersion includes a cross-linking agent which has functional groups which are reactive with the internal emulsifying agent's organic acid groups. This modified coating composition is then applied to a surface of the implantable medical device and dried as described below. The implantable medical device is then contacted with an aqueous solution or dispersion of an organic acid functional group-containing bio-active agent. This solution is applied over the polycarbonate-polyurethane top coat in the same or a different manner as the polycarbonate-polyurethane coating was applied to the substrate. The bio-active coating is then permitted to dry, thereby covalently bonding the organic acid functional group-containing bio-active agent to the polycarbonate-polyurethane top coat via the excess, unreacted functional groups of the cross-linking agent.

Bio-active agents for use in bio-compatible coatings include those known in the art. In the present invention, any bio-active agent may be used in the second coating provided that it contains at least one organic acid functional group in its structure which can react with the polyfunctional cross-linking agent and still retain its bio-active function.

The bio-active agent of the present invention may include, for example, thrombo-resistant agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof. Other useful bio-active agents include, for example, viral vectors and growth hormones such as Fibroblast Growth Factor and Transforming Growth Factor-$\beta$.

Furthermore, the bio-active agent of the present invention can include organic acid functional group-containing thrombo-resistant agents. For purposes of the present invention, such thrombo-resistant agents include heparin, heparin sulfate, hirudin, hyaluronic acid, chondroitin sulfate, dermatan sulfate, keratin sulfate, lytic agents, including urokinase and streptokinase their homologs, analogs, fragments, derivatives and pharmaceutical salts thereof.

Moreover, the bio-active agent of the present invention can also include organic acid functional group-containing antibiotics. For purposes of the present invention, such antibiotics include penicillins, cephalosporins, vancomycins, aminoglycosides, quinolones, polymyxins, erythromycins, tetracyclines, chloramphenicols, clindamycins, lincomycins, sulfonamides their homologs, analogs, fragments, derivatives, pharmaceutical salts and mixtures thereof.

Additionally, the bio-active agent of the present invention can also include organic acid functional group-containing anti-tumor agents. For purposes of the present invention, such anti-tumor agents include paclitaxel, docetaxel, alkylating agents including mechlorethamine, chlorambucil, cyclophosphamide, melphalan and ifosfamide; antimetabolites including methotrexate, 6-mercaptopurine, 5-fluorouracil and cytarabine; plant alkaloids including vinblastine, vincristine and etoposide; antibiotics including doxorubicin, daunomycin, bleomycin, and mitomycin; nitrosureas including carmustine and lomustine; inorganic ions including cisplatin; biological response modifiers including interferon; enzymes including asparaginase; and hormones including tamoxifen and flutamide their homologs, analogs, fragments, derivatives, pharmaceutical salts and mixtures thereof.

Still further, the bio-active agent of the present invention can include organic acid functional group-containing anti-viral agents. For purposes of the present invention, such anti-viral agents include amantadines, rimantadines, ribavirins, idoxuridines, vidarabines, trifluridines, acyclovirs, ganciclovirs, zidovudines, foscamets, interferons their homologs. analogs, fragments, derivatives, pharmaceutical salts and mixtures thereof.

In certain cases, such bio-active agents may also become lubricous upon contact with an aqueous medium. Such lubricity will depend on a number of factors, including the type of bio-active agent, its molecular weight, the exposure level to the aqueous medium, as well as, the presence of agents which facilitate wetting. In the present invention, the molecular weight of the bio-active agent can vary from, for example, about 3,000 to about 30,000 for heparin to an excess of 8,000,000 for hyaluronic acid.

The concentration of the bio-active agent will vary depending upon the particular agent used, its intended function and the chosen substrate. It is within the knowledge of one skilled in the art, knowing the above-referenced variables, to calculate appropriate bio-active agent concentrations for use in accordance with the present invention.

As set forth above, when used as a thrombo-resistant top coat for an implantable medical device, the polycarbonate-polyurethane composition is applied to a surface thereof and permitted to dry at a temperature below 120° C. Preferably, this drying takes place between about 10° C. to about 70° C. More preferably, this top coat is dried at ambient or room temperatures, such as for example, at or between about 15° C. and about 35° C.

The drying step for the optional second coating as described above is chosen based on the composition of the medical device, the polycarbonate-polyurethane composition and the bio-active agent. The selection of the appropriate driving temperature is within the skill of the art given the properties of the substrate and the compositional make up of the polycarbonate-polyurethane and bio-active agent coatings. Preferably, the drying steps take place well below 120° C. If desired, however, and compatible with the nature of the medical device to be coated, higher temperatures may be used, such as for example, when the substrate is metal.

Nevertheless, the present invention is particularly intended to be used to coat temperature-sensitive substrates using temperature sensitive bio-active agents. Thus, the optional bio-active agent, as well as the polycarbonate-polyurethane top coat are preferably dried at low temperatures, particularly at ambient or room temperatures, such as for example, at or between about 15° C. and about 35° C. In many cases, drying at about room temperature for about 12 hours will be adequate. Surface coatings formed in such a manner are long lasting, highly bio-active, anti-abrasive and, depending upon the bio-active agent used, may also be highly lubricious.

Obviously, the drying time will depend on the drying temperature used, higher drying temperatures requiring shorter drying times and lower drying temperatures requiring longer drying times. As set forth above, it is within the knowledge of a person skilled in the art to determine a suitable combination of drying temperatures and drying times for a specific coating and substrate.

Furthermore, the organic acid functional groups of the cross-linking agent do not necessarily have to have the same reactivity towards the organic acid functional groups of the polycarbonate-polyurethane composition and the bio-active agents, respectively. Moreover, the selection of drying conditions will be made with these reactivities in mind.

Still further, in the present invention, multiple layers of the polycarbonate-polyurethane coating, either alone or in combination with multiple layers of the bio-active agent coatings may be applied to the surface of an implantable medical device. It is within the skill of the art to determine appropriate drying times when multiple coatings are applied to an implantable medical device.

For purposes of the present invention, the term "medical device" or "medical devices" includes implantable medical devices, including endoprosthetic devices. Such devices include, for example, vascular and nonvascular stents, grafts and stent-graft combinations. Also included in the present invention are catheters and guide wires. Nonvascular stents encompassed by the present invention include, for example, esophageal stents, urinary stents, biliary stents, and colonic stents. Stents useful in the present invention include those which are balloon expandable and self-expanding. Superelastic, shaped memory materials, such a nitinol, are among those materials useful for the self-expanding type of stents.

The medical device of the present invention is made from any material which is suitable for implantation into the body of a mammal, such as a human, and to which the present bio-compatible coating compositions can bind. In particular, the present device can be a polymer, a non-polymer or mixtures thereof. Furthermore, the medical device of the present invention may include a combination of one or more polymers and/or one or more non-polymers.

The types of polymers which can be used to manufacture the present medical devices are quite diverse. Such polymers include both degradable and non-degradable polymers. The medical device of the present invention is made from, for example, non-degradable polymer compositions, such as, olefin polymers including polyethylene, polypropylene, polyvinyl chloride, polytetrafluoroethylene, polyvinyl acetate, polystyrene, poly(ethylene terephthalate), polyurethane, polyurea, silicone rubbers, polyamides, polycarbonates, polyaldehydes, natural rubbers, polyether-ester copolymers, styrene-butadiene copolymers and combinations thereof.

As set forth above, the medical device of the present invention can also be made from degradable polymer compositions including polysaccharides such as for example, methyl cellulose, hydroxymethyl cellulose, hydroxyethyl cellulose, hydroxypropyl cellulose, hydroxy-propylmethyl cellulose, hydroxypropylethyl cellulose, sodium carboxymethyl cellulose, hyaluronic acid, chondroitin sulfate, chitosan, dextran, xanthan, gellan, alginic acid, jota carrageenan; polypeptides such as for example, collagen, gelatin, elastin, albumin; and synthetic polymers such as for example, poly(vinyl alcohol), poly(lactic acid), polyglycolic acid, poly-$\epsilon$-caprolactone, polyanhydride their copolymers and mixtures thereof.

As set forth above, the medical device of the present invention can also be made from non-polymer compositions. Such compositions include, for example, ceramics, metals, glasses and combinations thereof. When the medical device is made from a metal, a variety of biocompatible metals may be utilized such as for example, stainless steel, nitinol, tantalum, titanium, gold, silver, their alloys and mixtures thereof.

In another embodiment of the present invention, there is provided a process for rendering a medical device bio-compatible. This process includes providing a substrate with a continuous surface coating of an aqueous emulsion or dispersion of a polycarbonate-polyurethane composition having at least one internal emulsifying agent, as previously described. The polycarbonate-polyurethane composition is then permitted to dry onto the substrate as previously described. Substrates treated in such a manner are provided with enhanced thrombo-resistance over the entire coated surface area.

When it is desired to add a bio-active agent coating on top of the polycarbonate-polyurethane top coat, the polycarbonate-polyurethane top coat is modified by selecting an internal emulsifying agent which contains at least one organic acid functional group. An excess of a polyfunctional cross-linking agent which is reactive with these organic acid functional groups is then added to the aqueous polycarbonate-polyurethane emulsion or dispersion. Thus, to enhance, augment or modify the anti-thrombogenic nature of a substrate coated as described above, a bio-active agent as previously described can optionally be attached to the substrate via the excess polyfunctional cross-linking agent. In particular, the polycarbonate-polyurethane coated substrate is further contacted with a bio-active agent to form a continuous coating thereon. The bio-active agent is then dried as described previously to bond covalently the bio-active agent to the polycarbonate-polyurethane composition via the excess polyfunctional cross-linking agent. Thus, in this embodiment, the polycarbonate-polyurethane coating composition functions as an effective undercoat or primer to which the bio-active agent is applied.

In another embodiment of the present invention, there is provided a coating for enhancing the bio-activity of a surface of a medical device. The coating is formed from an aqueous emulsion or dispersion of a polycarbonate-polyurethane composition having an organic acid functional group and an excess of a polyfunctional cross-linking agent as previously described. As set forth above, this composition is attached to the surface of the medical device and is reactive with bio-active agents also as described previously.

In yet a further embodiment of the present invention, a medical device is provided with enhanced thrombo-resistance. This medical device includes a substrate as described previously which has a thrombo-resistant coating attached thereto. As set forth above, this thrombo-resistant coating is attached to the substrate surface and contains an aqueous emulsion or dispersion of a polycarbonate-polyurethane composition having an internal emulsifying agent. This polycarbonate-polyurethane composition is prepared, for example, by reacting a polyfunctional isocyanate with a polycarbonate diol. As set forth above, such compositions are normally obtained from commercial sources.

In yet another embodiment of the present invention, a medical device is provided which has a surface rendered bio-compatible by means of a first coating layer as previously described. This first coating layer includes a polycarbonate-polyurethane composition containing an internal emulsifying agent. When it is desired to use the polycarbonate-polyurethane composition as a top coat for a bio-active agent coating, the internal emulsifying agent is selected to have at least one organic acid functional group. This composition may also include a polyfunctional cross-linking agent.

As set forth above, a second coating layer may also be applied to the above-referenced medical device. In particular, the second coating layer includes a bio-active agent covalently bonded to the first coating layer. The second coating layer is formed by the process which has been described previously.

In still a further embodiment, a medical device is provided which has a surface coated with a bio-active layer. This bio-active layer is the reaction product of a polycarbonate-polyurethane first layer as described above which includes a polyfunctional cross-linking agent and a bio-active agent also as previously described.

The invention will now be further illustrated in the following non-limiting examples representing presently preferred embodiments of the invention.

EXAMPLE 1

An aqueous dispersion or emulsion is prepared by adding the following ingredients successively to a glass beaker under proper agitation until thoroughly mixed.

NeoRez R985: 250 ml

Water: 250 ml 0.5% Fluorad FC-129 stock solution: 10 ml (prepared by diluting 1 ml Fluorad FC-129 in 100 ml of water)

34% $NH_4OH$: 4 ml

An implantable medical device is dipped into this aqueous dispersion and then withdrawn. Excess amounts of the aqueous composition are allowed to drip off and the coated stent is then dried at room temperature for 12 hours. The coated implantable medical device exhibits superior thrombo-resistance when placed within the body of a mammal.

EXAMPLE 2

An aqueous dispersion or emulsion is prepared by adding the following ingredients successively to a glass beaker under proper agitation until thoroughly mixed.

NeoRez R985: 250 ml

Water: 250 ml 0.5% Fluorad FC-129 stock solution: 10 ml (prepared by diluting 1 ml Fluorad FC-129 in 100 ml of water)

34% $NH_4OH$: 4 ml

NeoCryl CX 100: 20 ml

An implantable medical device is dipped into this aqueous dispersion and then withdrawn. Excess amounts of the aqueous composition are allowed to drip off and the coated device is then dried at room temperature for 12 hours.

A bio-active coating composition is prepared as follows:

1.2% aqueous solution of Heparin: 400 ml

This aqueous bio-active composition is prepared by adding an appropriate amount of heparin powder to water under agitation for several hours to obtain a clear homogeneous solution.

The medical device is dipped in the polycarbonate-polyurethane solution and then air dried for 10 minutes. Immediately thereafter, the polycarbonate-polyurethane coated implantable medical device is then dipped into the aqueous heparin solution and then withdrawn. Excess amounts of the aqueous bio-active composition are allowed to drip off and the coated stent is then air dried for 10 minutes. The coated implantable medical device exhibits superior thrombo-resistant properties when placed within the body of a mammal.

EXAMPLE 3

The implantable medical device of EXAMPLE 2 is prepared with the exception that an antibiotic agent is substituted for the heparin. The coated implantable medical device exhibits superior anti-biotic properties when placed within the body of a mammal.

EXAMPLE 4

The implantable medical device of EXAMPLE 2 is prepared with the exception that an antitubior agent is substituted for the heparin. The coated implantable medical device exhibits superior antitumor properties when placed within the body of a mammal.

EXAMPLE 5

The implantable medical device of EXAMPLE 2 is prepared with the exception that an antiviral agent is substituted for the heparin. The coated implantable medical device exhibits superior antiviral properties when placed within the body of a mammal.

EXAMPLE 6

The implantable medical device of EXAMPLE 2 is prepared with the exception that an anti-angiogenic agent is substituted for the heparin. The coated implantable medical device exhibits superior anti-angiogenic properties when placed within the body of a mammal.

EXAMPLE 7

The implantable medical device of EXAMPLE 2 is prepared with the exception that an angiogenic agent is substituted for the heparin. The coated implantable medical device exhibits superior angiogenic properties when placed within the body of a mammal.

EXAMPLE 8

The implantable medical device of EXAMPLE 2 is prepared with the exception that an anti-inflammatory agent is substituted for the heparin. The coated implantable medical device exhibits superior anti-inflammatory properties when placed within the body of a mammal.

EXAMPLE 9

The implantable medical device of EXAMPLE 2 is prepared with the exception that a cell cycle regulating agent is substituted for the heparin. The coated implantable medical device exhibits superior cell cycle regulating properties when placed within the body of a mammal.

The invention being thus described, it will be obvious that the same may be varied in many ways. Such variations are not to be regarded as a departure from the spirit and scope of the invention and, all such modifications are intended to be included within the scope of the following claims.

What is claimed is:

1. A medical device having a surface, said surface having a biocompatible coating formed thereon, the coating having a polyurethane-polycarbonate composition free of organic solvent, the coating containing an internal emulsifying agent with one or more organic acid functional groups and an excess of a polyfunctional cross-linking agent, said medical device adapted for insertion into a mammalian body, said coating formed on an external surface of said medical device.

2. The medical device of claim 1, wherein said one or more organic acid functional groups are selected from the group consisting of fee carboxylic acid, free sulfonic acid, free phosphoric acid and combinations thereof.

3. The medical device of claim 1, wherein said polyfunctional cross-linking agent is selected from the group consisting of polyfunctional aziridines, polyfunctional carbodiimides and combinations thereof.

4. The medical device of claim 1, further comprising a bio-active agent selected from the group consisting of thrombo-resistant agents, anti-tumor agents, growth hormones, antiviral agents, anti-angiogenic agents, angiogenic agents, anti-mitotic agents, anti-inflammatory agents, cell cycle regulating agents, genetic agents, hormones, chemically modified equivalents and combinations thereof.

5. The medical device of claim 1, wherein said surface is selected from the group consisting of polymers, ceramics, metals, glasses and combinations thereof.

6. The medical device of claim 1, wherein said surface is selected from the group consisting of polyethylene, polypropylene, polyvinyl chloride, polytetrafluoroethylene, polyvinyl acetate, polystyrene, poly(ethylene terephthalate), polyurethane, polyurea, silicone rubbers, polyamides, polycarbonates, polyaldehydes, natural rubbers, polyether-ester copolymers, styrene-butadiene copolymers and combinations thereof.

* * * * *

UNITED STATES PATENT AND TRADEMARK OFFICE
CERTIFICATE OF CORRECTION

PATENT NO. : 6,723,121 B1  
DATED : April 20, 2004  
INVENTOR(S) : Zhong

It is certified that error appears in the above-identified patent and that said Letters Patent is hereby corrected as shown below:

<u>Title page,</u>  
Item [56], References Cited, U.S. PATENT DOCUMENTS, the following reference should be cited:

-- 5,623,772 A     5/1997     Alcime et al. --

FOREIGN PATENT DOCUMENTS, the following references should be cited:

-- EP     0404515 A2    12/1990  
   JP     58021415 A     2/1983 --

OTHER PUBLICATIONS, the following reference should be cited:

-- Niwa Makolo, "Manufacture of aqueous self-emulsifying urethane polymer dispersions," Chemical Abstracts, vol. 130, Columbus, Ohio, U.S.: abstract no. 4456 (XP002091442 & JP 10 287722 A; Toa Gosei Chemical Industry Co., Ltd., Japan). --

Signed and Sealed this

Twenty-fourth Day of August, 2004

JON W. DUDAS  
*Director of the United States Patent and Trademark Office*